US009945828B1

(12) United States Patent
Poling et al.

(10) Patent No.: US 9,945,828 B1
(45) Date of Patent: Apr. 17, 2018

(54) AIRBORNE MULTISPECTRAL IMAGING SYSTEM WITH INTEGRATED NAVIGATION SENSORS AND AUTOMATIC IMAGE STITCHING

(71) Applicant: Sentek Systems LLC, Lakeville, MN (US)

(72) Inventors: Bryan T. Poling, Minneapolis, MN (US); Kimberly A. Salant, Lakeville, MN (US); Theodore C. Poling, Eden Prairie, MN (US); Christopher A. Launer, Crystal, MN (US)

(73) Assignee: SENTEK SYSTEMS LLC, Lakeville, MN (US)

( * ) Notice: Subject to any disclaimer, the term of this patent is extended or adjusted under 35 U.S.C. 154(b) by 158 days.

(21) Appl. No.: 14/921,335

(22) Filed: Oct. 23, 2015

(51) Int. Cl.
| | |
|---|---|
| *G06K 9/00* | (2006.01) |
| *G01N 33/00* | (2006.01) |
| *G06T 7/00* | (2017.01) |
| *H04N 7/18* | (2006.01) |
| *G06T 11/60* | (2006.01) |
| *H04N 5/232* | (2006.01) |
| *H01L 27/146* | (2006.01) |

(52) U.S. Cl.
CPC ....... *G01N 33/0098* (2013.01); *G06T 7/0004* (2013.01); *G06T 7/0024* (2013.01); *G06T 11/60* (2013.01); *H01L 27/14645* (2013.01); *H01L 27/14649* (2013.01); *H04N 5/23245* (2013.01); *H04N 7/185* (2013.01); *G06T 2207/30188* (2013.01)

(58) Field of Classification Search
None
See application file for complete search history.

(56) References Cited

U.S. PATENT DOCUMENTS

| | | |
|---|---|---|
| 5,798,786 A | 8/1998 | Lareau et al. |
| 5,894,323 A | 4/1999 | Kain et al. |
| (Continued) | | |

FOREIGN PATENT DOCUMENTS

| | | |
|---|---|---|
| CN | 103557841 A | 2/2014 |
| EP | 1313308 B1 | 2/2009 |
| (Continued) | | |

OTHER PUBLICATIONS

Peterson, et al., "G93-1171 Using a Chlorophyll Meter to Improve N Management," Jan. 1993, 7 pages.
(Continued)

*Primary Examiner* — Weiwen Yang
(74) *Attorney, Agent, or Firm* — Patterson Thuente Pedersen, P.A.

(57) ABSTRACT

A self-contained UAV sensor payload and on-board or off-board hardware and software for precision agriculture. The invention combines multiple cameras and navigation sensors to create a system for automatically collecting, geo-referencing, and stitching red, green, blue, and near infrared imagery and derived vegetation indices. The invention is able to produce all of these quantities in a single flight. The tight integration with integrated navigation sensors eliminates the need for integration with external sensors or avionics hardware and enables innovative solutions to image processing and analysis which greatly improve accuracy, processing speed, and reliability over alternative approaches.

18 Claims, 13 Drawing Sheets

(56) References Cited

U.S. PATENT DOCUMENTS

| | | | |
|---|---|---|---|
| 6,160,902 A | 12/2000 | Dickson et al. | |
| 6,597,818 B2 | 7/2003 | Kumar et al. | |
| 6,928,194 B2 | 8/2005 | Mai et al. | |
| 7,019,777 B2 | 3/2006 | Sun | |
| 7,557,832 B2 | 7/2009 | Lindenstruth et al. | |
| 7,725,257 B2 | 5/2010 | Strelow et al. | |
| 8,115,801 B2 | 2/2012 | Mei et al. | |
| 8,411,133 B2 | 4/2013 | Kim et al. | |
| 8,411,961 B1 | 4/2013 | Jin | |
| 8,693,806 B2 | 4/2014 | Acree | |
| 8,761,439 B1 | 6/2014 | Kumar et al. | |
| 8,831,290 B2 | 9/2014 | Ramalingam et al. | |
| 8,991,758 B2 | 3/2015 | Earon | |
| 9,046,759 B1 | 6/2015 | Tarlinton et al. | |
| 9,049,391 B2 | 6/2015 | Venkataraman et al. | |
| 9,555,883 B1* | 1/2017 | Navot | B64C 39/02 |
| 2005/0157181 A1 | 7/2005 | Kawahara et al. | |
| 2009/0059018 A1 | 3/2009 | Brosnan | |
| 2011/0142132 A1* | 6/2011 | Tourapis | H04N 19/597 |
| | | | 375/240.16 |
| 2012/0086727 A1 | 4/2012 | Korah et al. | |
| 2013/0258044 A1 | 10/2013 | Betts-LaCroix | |
| 2014/0012732 A1* | 1/2014 | Lindores | A01B 79/005 |
| | | | 705/37 |
| 2014/0098242 A1 | 4/2014 | Sharma et al. | |
| 2014/0246538 A1* | 9/2014 | Morris | B64C 27/02 |
| | | | 244/17.13 |
| 2014/0300775 A1 | 10/2014 | Fan et al. | |
| 2015/0041598 A1* | 2/2015 | Nugent | H02J 17/00 |
| | | | 244/53 R |
| 2015/0254800 A1* | 9/2015 | Johnson | C05C 11/00 |
| | | | 382/141 |
| 2016/0364989 A1* | 12/2016 | Speasl | G08G 5/0034 |

FOREIGN PATENT DOCUMENTS

| | | |
|---|---|---|
| JP | 5078589 B2 | 11/2012 |
| WO | WO 2014/162044 A1 | 10/2014 |
| WO | WO 2015/040917 A1 | 3/2015 |

OTHER PUBLICATIONS

Carter, "Responses of Leaf Spectral Reflectance to Plant Stress," Aug. 2015, 6 pages.

* cited by examiner

AIRBORNE MULTISPECTRAL IMAGING SYSTEM WITH INTEGRATED NAVIGATION SENSORS AND AUTOMATIC IMAGE STITCHING

TECHNICAL FIELD

Embodiments relate to arrangements of cameras and other sensors aboard an unmanned aerial vehicle (UAV) for use in agricultural settings.

BACKGROUND

Agricultural crops are often grown on farms which are too large for an individual to continuously monitor. As such, methods and systems for monitoring crops have been developed to reduce the chances of crop damage to some portion of a field due to, e.g., too little or too much water or fertilizer. Furthermore, it is important to discover damaging insects, fungi, or other blight as soon as possible, to prevent their spread to the rest of the field.

In many cases, crop damage affects the reflectance of leaves. As described in Gregory A. Carter, Responses of Leaf Spectral Reflectance to Plant Stress, 80(3) American Journal of Botany 239-243 (1993), not only does the net reflectance change, but the spectrum of reflectance also changes. In particular, based on spectral reflectance regression analysis, and vegetation index analysis including but not limited to the Normalized Difference Vegetation Index $NDVI=(NIR-R)/(NIR+R)$, where NIR is the near infrared reflectance and R is the red reflectance, it is often possible to determine not only whether a plant is stressed, but in fact what type of stress that plant is undergoing. For example, different spectra are reflected from leaves suffering from competition, herbicide, a pathogen, ozone, insufficient mycorrhizae, barrier island environment, senescence, and dehydration. An excess of fertilization could cause a different NDVI ratio compared to an absence of water, both of which are different from a healthy plant. Nitrogen sufficiency is strongly correlated with particular, readily identifiable vegetation indices including but not limited to the Normalized Difference Vegetation Index (NDVI), the Green Normalized Vegetation Index (GNDVI), the Green Ratio Vegetation Index (GRVI), and the Normalized Green (NG) index.

Indicators of overall plant health in a region have been measured for several decades through the Landsat satellite program. Landsat images can provide information regarding regional drought, insect infestations, or good health. The satellites that provide Landsat images have a return frequency of 16 days, but the relevant reflectance data can only be captured if the satellite happens to be over a particular field during daylight hours, without significant cloud cover. As such, there can often be a relatively long time period (weeks) between opportunities to measure the reflectance of a particular field. Generally it is desirable to discover abnormal reflectance very quickly to avoid giving insects, fungi, or other undesirable contamination a chance to establish themselves in the field.

Furthermore, Landsat images do not provide high enough resolution to identify some types of blight or insect damage until they spread across a field and effect large areas. Generally, it is desirable to discover abnormal results in very small areas, even down to a leaf-by-leaf analysis, so that diseases with a known spectral profile can be identified and addressed before they spread to the point where a Landsat satellite would detect them.

In recent years, agricultural unmanned aerial vehicles (UAVs) have been used to acquire some data on crop growth and health. Satellites have periodic, fixed opportunities to image a given location, and those opportunities may be rendered useless due to cloud cover. UAVs, by contrast, can collect data on demand whenever conditions permit, resulting in more timely access to critical information. UAVs have their own challenges, however, including susceptibility to wind gusts. Furthermore, tasks such as aligning images between multiple cameras, computing vegetation indices, and stitching RGB, Near Infrared, and Vegetation Index Images into mosaics, can be computationally expensive. For this reason these activities are often performed in post-processing. Often a UAV must make multiple passes through a field in order to acquire RGB and Near Infrared images and GPS coordinates, then combine these results later, slowing the process and providing low resolution, as well as potentially introducing errors into the acquired data.

SUMMARY

According to embodiments, a combination of cameras and other components are arranged to contemporaneously measure Visible (VIS) red, green, blue (RGB), and Near Infrared (NIR) spectra of a field in the same flight of a UAV. The cameras can provide imagery with ground sampling distances on the order of 1 cm, in some embodiments, by aligning VIS and NIR camera images to sub-pixel level alignment accuracy, computing vegetation index images using the aligned imagery, and stitching the VIS, NIR, and Vegetation Index (VI) image data collected from a single flight into image mosaics of the fields that were flown. Furthermore, by arranging the cameras on a UAV, the aforementioned problems with scan frequency from satellite imagery are obviated and scan data can be acquired on-demand.

In embodiments, an Unmanned Aerial Vehicle (UAV) can be outfitted with both Visible and Near Infrared (NIR) cameras, driven by a common processor. VIS and NIR data that are concurrently measured can then be stitched together into VIS, NIR and Vegetation Index (VI) mosaics. In various embodiments, the common processor can also operate position and/or angle sensors such as magnetometers, gyros, accelerometers, pressure sensors and a GPS system. Using position data, orientation data, and feature matching between images the system stitches together RGB, NIR, and Vegetation Index images to provide a precise, accurate, high-speed, on demand scan of the field.

The above summary of the invention is not intended to describe each illustrated embodiment or every implementation. The detailed description and claims that follow more particularly exemplify these embodiments.

Figure 1:
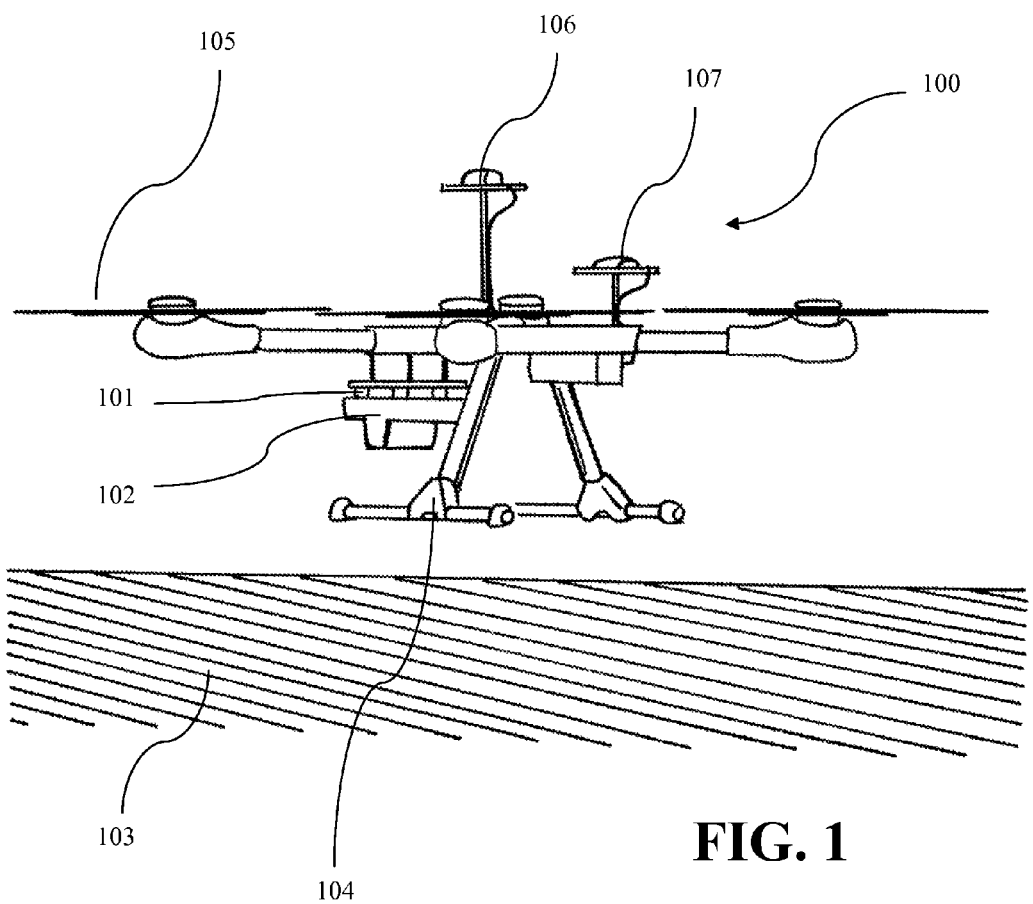
FIG. 1 is a perspective view of a multi-rotor unmanned aerial vehicle and the mounted multi-spectral camera system according to an embodiment.

While embodiments are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the appended claims.

DETAILED DESCRIPTION

As depicted in FIG. 1, 100 is a multi-rotor platform hovering over an irrigated potato field 103, but field could contain any crop type or other foliage, including, for example, corn, soybean, wheat or any type of fruit tree, vine, nut, vegetable or tropical fruit. Multi-rotor platform 100 can be any airborne vehicle capable of carrying a payload and is mounted with vibration isolators 101 and enclosed in a mechanical enclosure 102 in an embodiment. Multi-rotor Unmanned Aerial Vehicles (UAVs) are ideal platforms for remote sensing applications due to their ability to withstand high wind environments as well as the ease of use to entry level UAV operators for take-off and landing events. Additionally, multi-rotors can be used when hovering or low-speed flight is desirable for specific high resolution applications. The multi-rotor depicted in FIG. 1. includes high efficiency propellers 105, landing gear 104, and the multi-rotor aerial vehicle mission critical GPS system 107. The multi-spectral camera UAV payload includes an integrated GPS receiver 132 and the system's corresponding GPS antenna 106 is depicted in FIG. 1.

Figure 2:
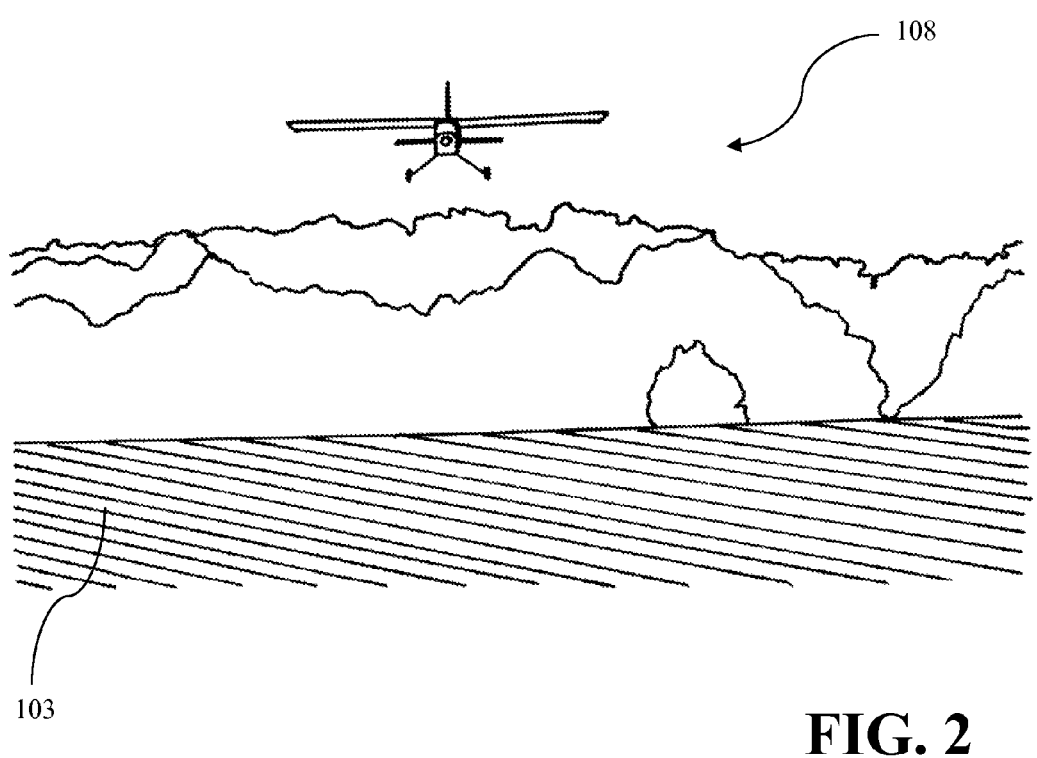
FIG. 2 is a perspective view of a fixed wing unmanned aerial vehicle and the installed multi-spectral camera system according to an embodiment.
Figure 3:
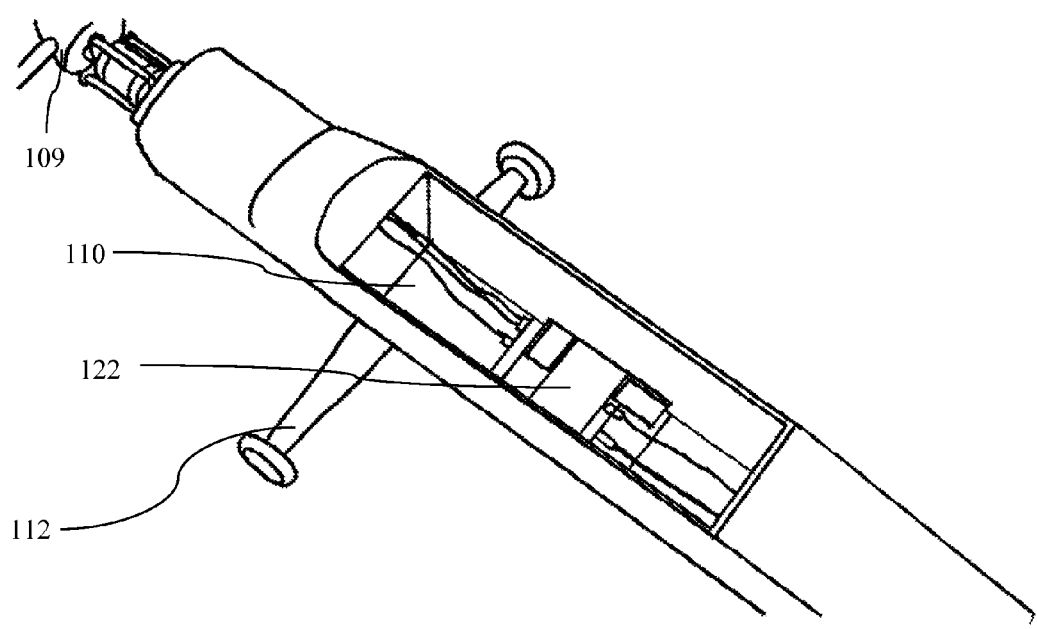
FIGS. 3 and 4 are perspective views of the multi-spectral camera system installed in a typical fixed wing unmanned aerial vehicle payload bay according to an embodiment.
Figure 4:
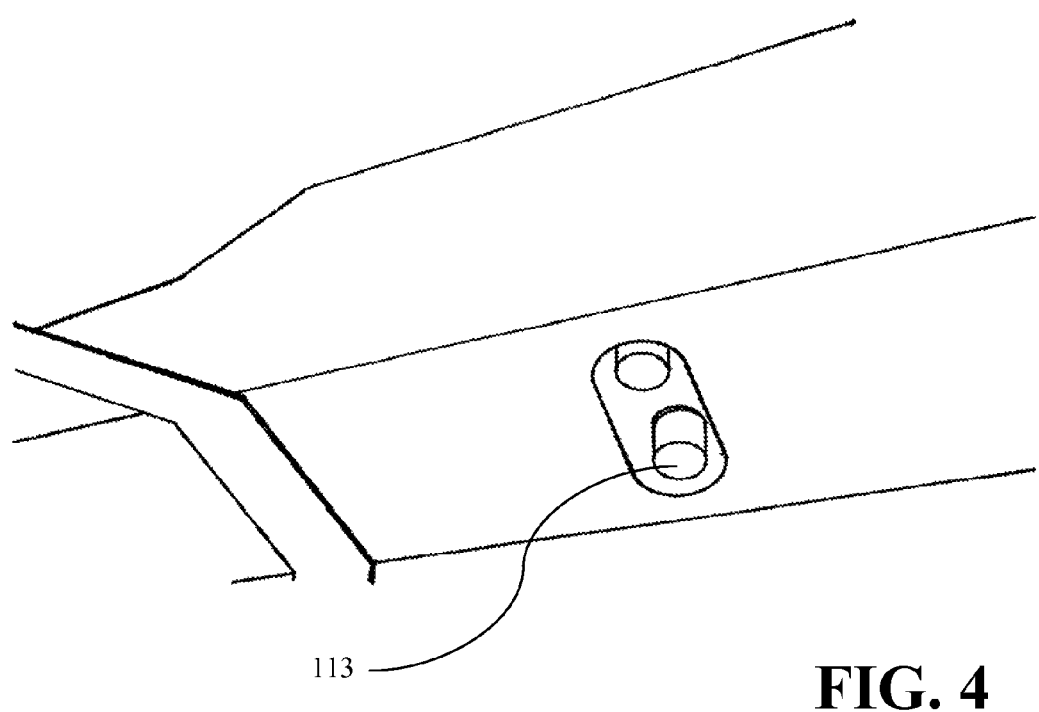

FIGS. 2, 3, and 4 depict a fixed wing aerial vehicle platform 108 integrated with the multi-spectral camera system 122 in the platform payload bay 110. This is a typical installation where the camera lenses 125a and 125b are recessed 113 inside the payload bay for protection from the elements. FIG. 3 illustrates a motor and propeller system 109 for a fixed wing platform and standard landing gear 112. FIG. 4 depicts the underside of the payload bay with the camera lenses completely recessed 113.

Figure 5:
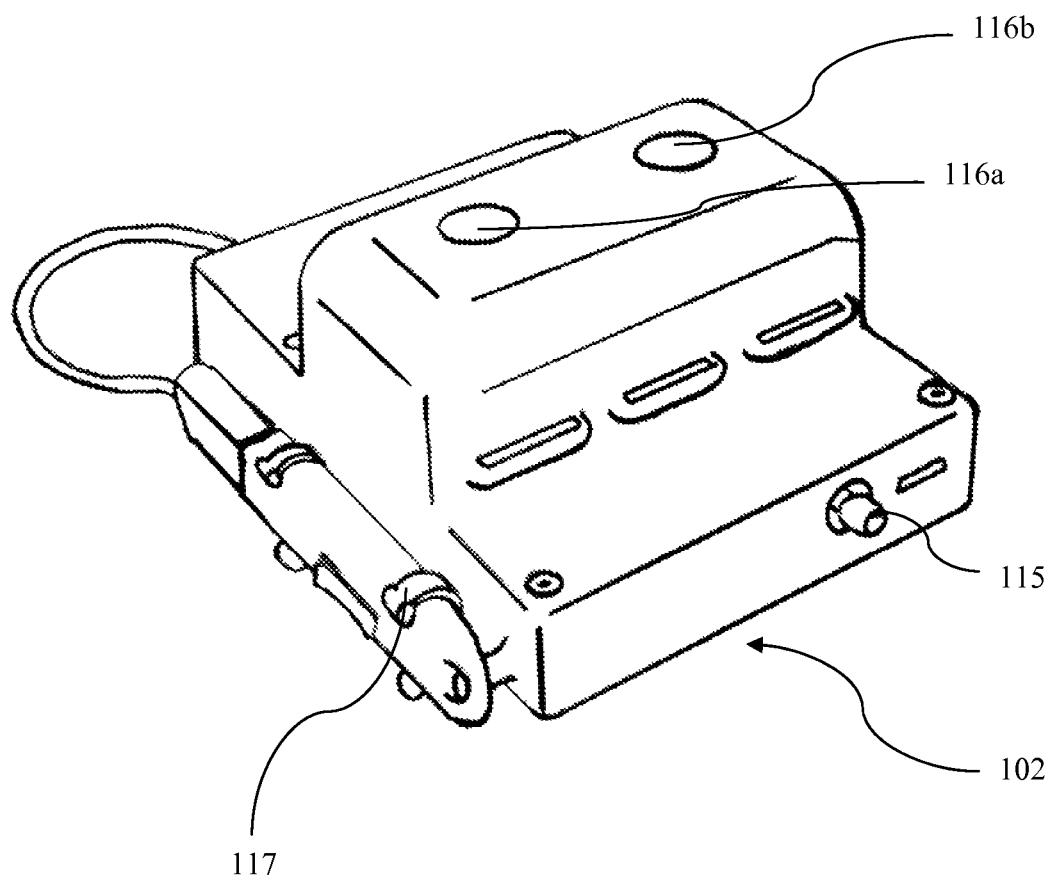
FIGS. 5 and 6 are perspective views of the multi-spectral camera system encased in the mechanical enclosure according to an embodiment.
Figure 6:
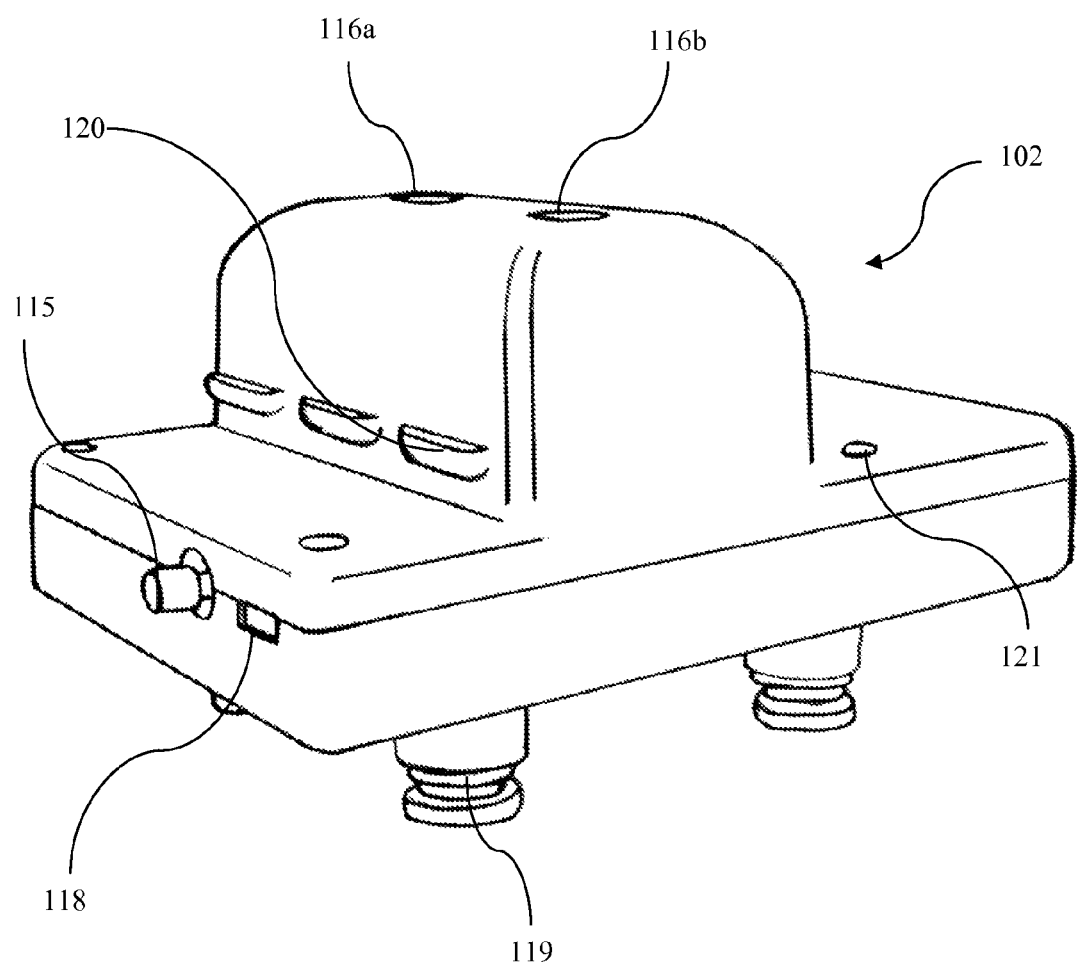
Figure 7:
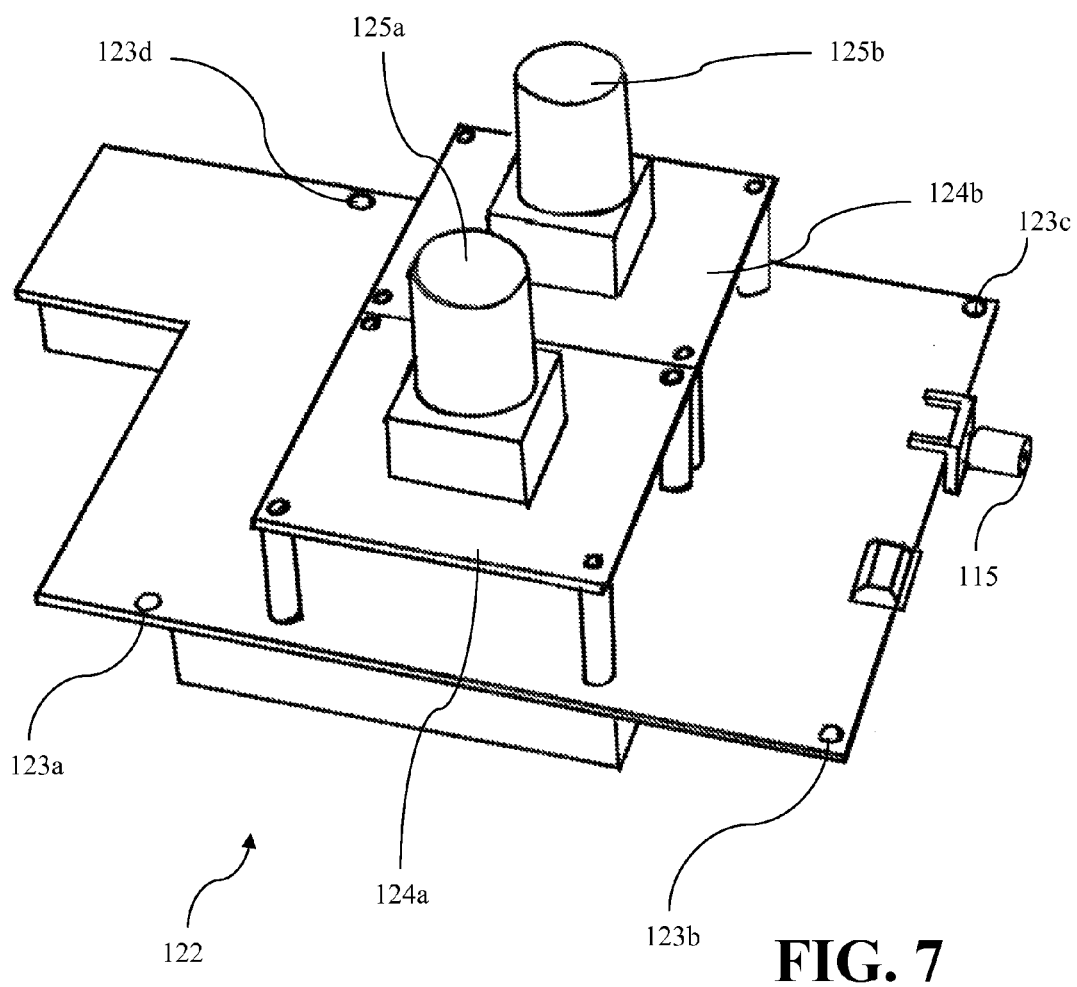
FIGS. 7, 8, and 9 are partial perspective views of the multi-spectral camera system depicted without a housing according to an embodiment.

FIGS. 5 and 6 depict specifics about the mechanical enclosure 102 with an integrated mounting configuration. FIG. 5 depicts how, in this embodiment, the multi-spectral camera system GPS antenna 106 connects to the hardware invention through a high frequency 50-Ohm SMA connector 115 and high frequency RF coaxial cable 144. UAVs used in remote sensing for precision agriculture are exposed to the elements. In an embodiment the mechanical enclosure 102 is designed to withstand high vibration environments through utilizing vibration isolators 119 built into the bottom of the enclosure as depicted in FIG. 6. Additionally, the UAV will be flown in full sunlight and therefore overheating due to sun exposure is of concern. Therefore the mechanical enclosure includes a built in air ventilation system 120 on both sides of the enclosure in an embodiment to ensure airflow over the processor for internal cooling in flight. In an embodiment camera apertures 116a, 116b for the lenses are recessed inside the mechanical enclosure to ensure the payload is protected in the event of a crash landing of the UAV system. Enclosure opening 118 is provided for the remote LED cable 141 to secure to the General Input Output (GPIO) connector 126. This enables the remote LED board 140 to connect to the payload. The remote LED board is used to visually indicate the system health to the user for systems that are embedded inside payload bays. Key information is displayed with color coded LEDs for example, GPS acquisition, all images stored correctly to the storage media after flight, and if there is an error prior to takeoff. Four lock nuts and bolts secure through the mechanical enclosure as illustrated at reference number 121 and align with the four mounting holes in the system 123a, 123b, 123c, 123d to secure the payload to the mechanical enclosure in a high vibration environment. On the side of the mechanical enclosure is a built in clip mechanism 117 designed to secure the USB storage device during flight.

Figure 8:
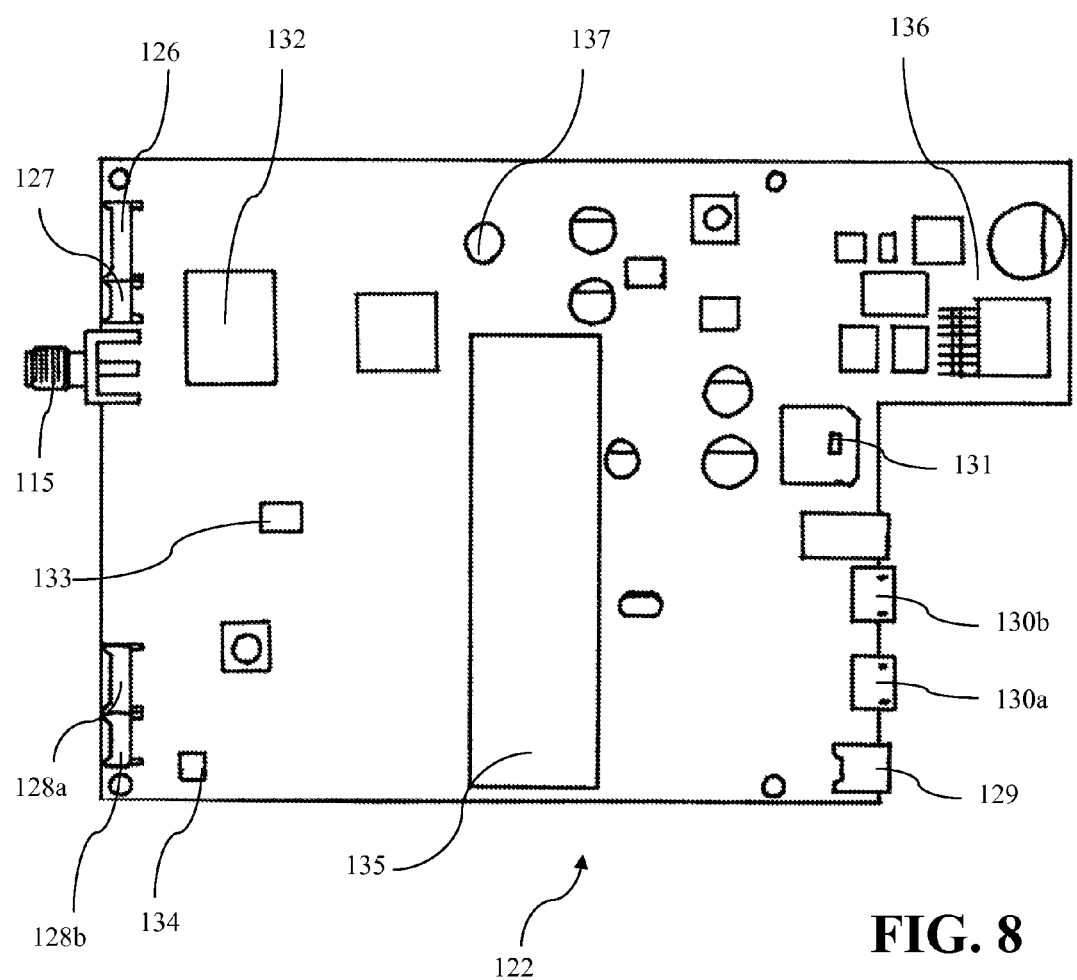
Figure 9:
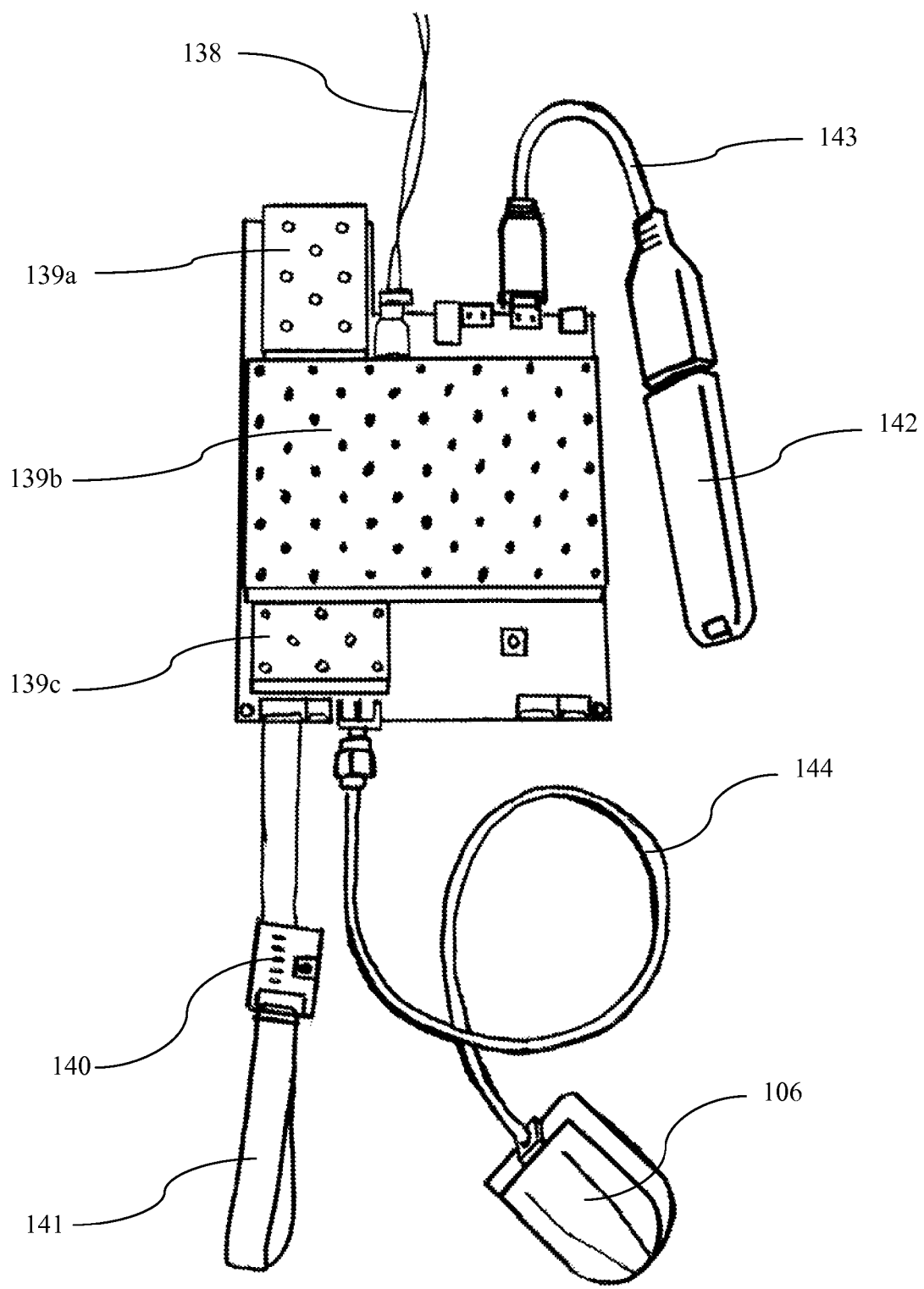
Figure 10:
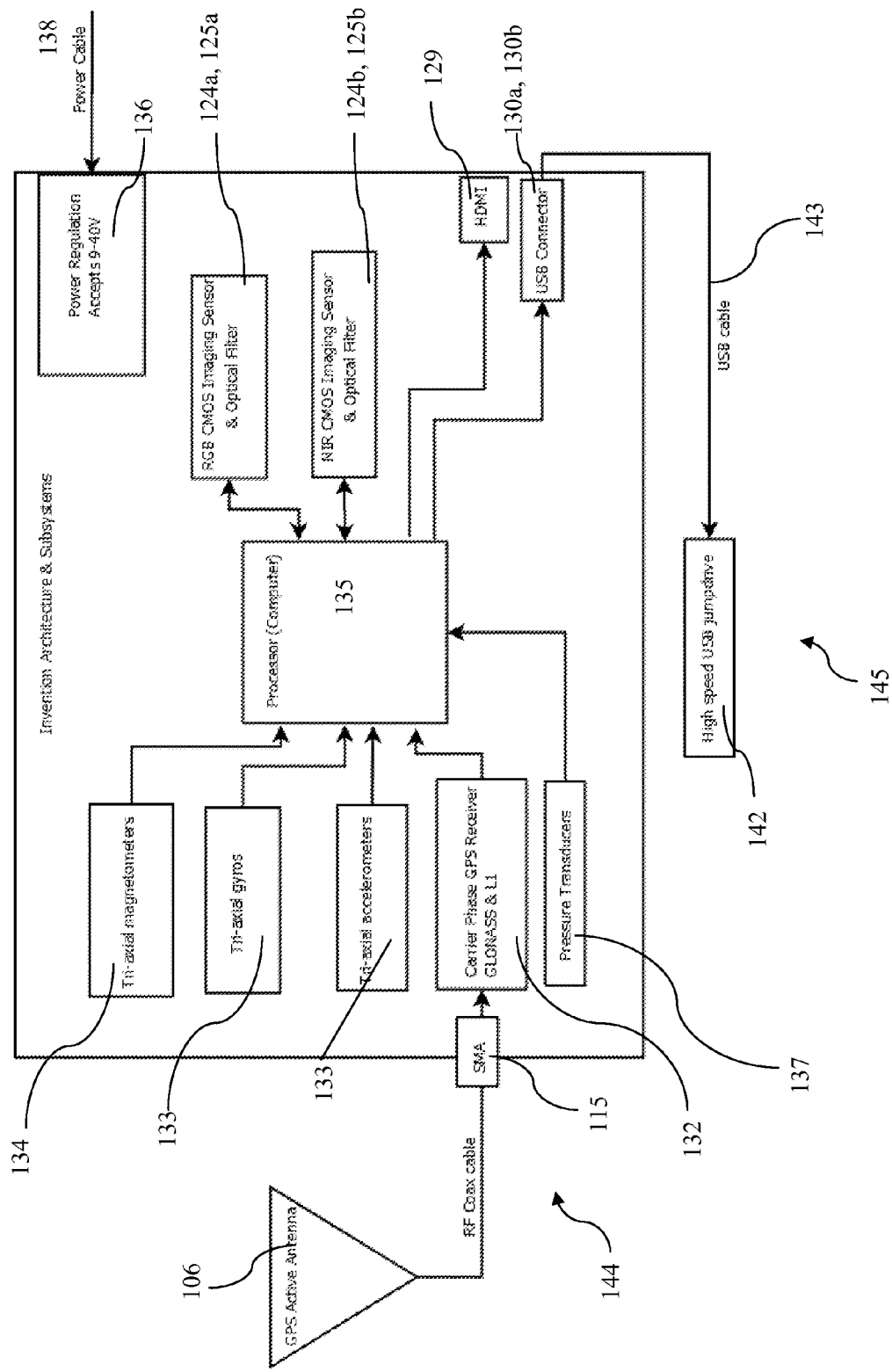
FIG. 10 is a system level block diagram outlining the architecture and main components of the multi-spectral camera system according to an embodiment.

FIGS. 7, 8, 9, and 10 depict the hardware portion 122 of the invention, which is a multi-spectral camera sensor system that is a fully self-contained UAV sensor payload for use in agriculture, with accompanying processing and analysis software 146. A system level block diagram 145 outlining the architecture and subsystems of the invention is depicted in FIG. 10. The sensor is comprised of the following:

Gyroscopes, 133
Accelerometers, 133
Magnetometers, 134
A carrier-phase GPS receiver, 132
Pressure transducers, 137
An RGB imager, including RGB CMOS camera subsystem 124a and RBG lenses and optics configuration 125a with built in optical filters
An NIR imager, including NIR CMOS camera subsystem 124b and NIR lenses and optics configuration 125b with built in optical filters
An integrated processor including a heatsink and supporting hardware, 135
Onboard power regulation that accepts 9-40 VDC input, 136
An incident light sensor (ILS)—on some embodiments that can be connected to expansion port 1 connector 128a or expansion port 2 connector 128b
On some embodiments an air temperature sensor can be connected to air temperature connector 127 which is an air temperature connector FIGS. 8 and 9 depict the hardware invention connectors and corresponding subsystems.

FIG. 8 illustrates the power connector 131 that includes built in polarity agnostic circuitry and FIG. 9 illustrates the cable 138 used to power the invention that connects to power connector 131. In an embodiment the onboard power regulation is designed to accept input from standard RC UAV batteries in the range of 9-40 VDC. The polarity agnostic circuitry is specifically designed for ease of use for the UAV integrator by allowing power and ground to be connected to the systems power inputs in any order. FIG. 8 depicts micro USB connectors 130a, 130b that directly connect to the hardware invention and, for example, can connect to a USB storage device for transferring collected imagery and all sensor data. In an embodiment a micro USB connector connects the high-speed storage media device 142 through a USB to micro USB cable 143. The storage media device is used to collect all sensor data and images during operation. Micro HDMI connector 129 is utilized for sensor calibration in one embodiment. FIG. 9 depicts electromagnetic interference (EMI) shields 139a (for power regulation section), 139b (for CPU and supporting subsystems), 139c (for GPS subsystem). The EMI shields ensure other operational systems on the unmanned aerial vehicle (i.e. Radio frequency communications, oscillators, and other printed circuit boards that are emitting interference) do not interfere with the hardware invention.

Figure 12:
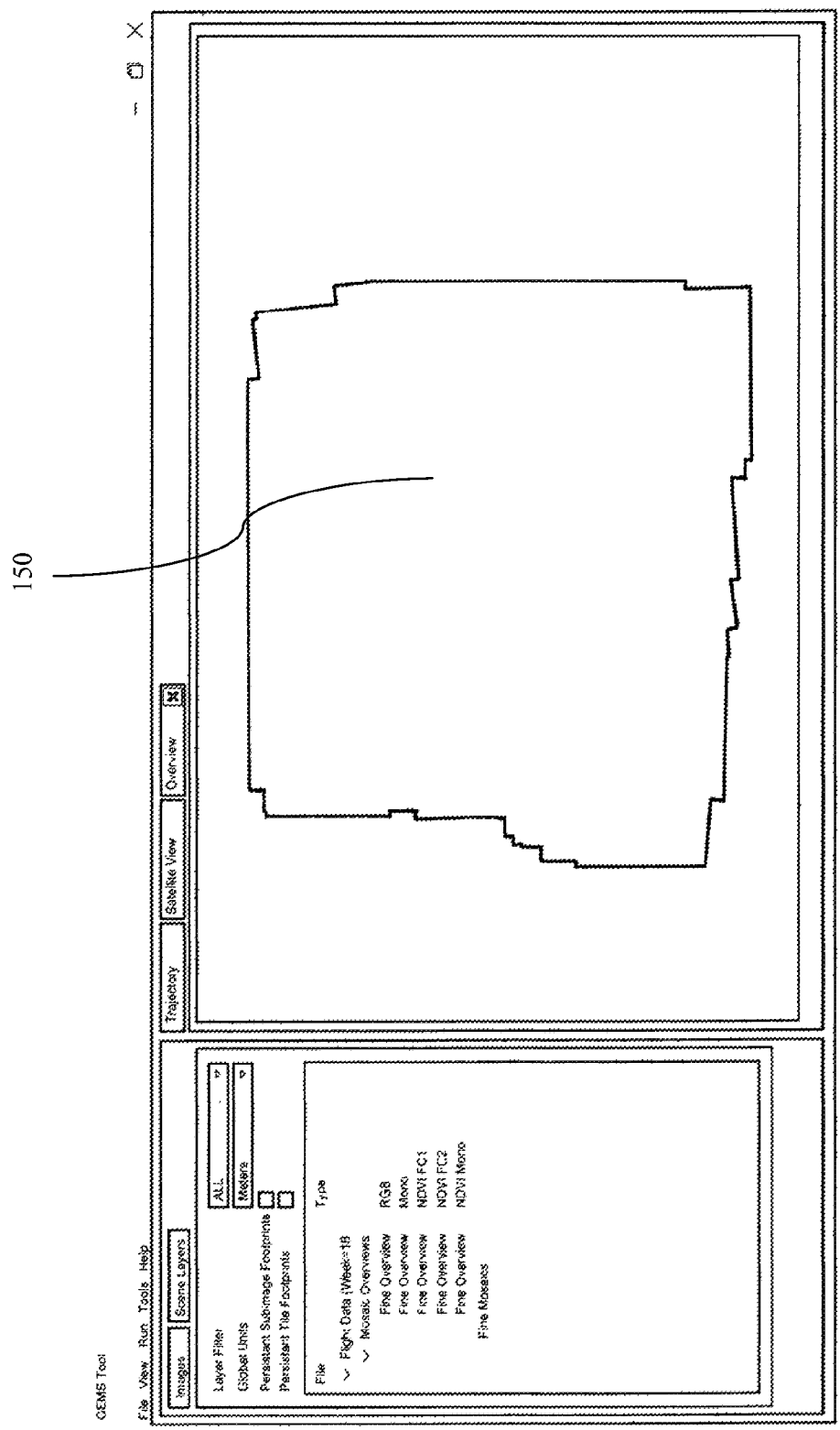
FIG. 12 depicts the software component of an embodiment, showing the main user interface and an RGB mosaic of a UAV flight.

The sensor system 122, in its primary mode, will autonomously detect when the host vehicle has taken off and it will begin recording imagery and sensor data from all on-board sensors outlined above. It will continue recording data until it autonomously detects when the host vehicle lands, at which point it will finalize the recording and store the data to the high-speed USB storage device 142. An alternate, manual recording mode is also available. The post-processing software 146 component of the invention processes the collected sensor data and imagery and produces RGB, NIR, and vegetation index photo-mosaics 150 illustrated in FIG. 12 and associated analysis based on the data collected in a single flight. The RGB and NIR photo-mosaics and vegetation index mosaics are geo-registered and provide insight into crop health, potential problem areas in a field, and possible causes of plant stress. The invention makes it possible to monitor crops accurately, remotely, easily, and on demand. Referring to FIG. 12, the mosaic overview 150 allows visualizations in different false color maps as well as customized color maps.

The software component of the invention can exploit the on-board navigation sensors, 133, 134, 137, 132, 127, to accelerate image stitching. Such software can also automatically employ multi-threading and GPU acceleration when supported by the end user's hardware. Combined, these make it fast enough to run on commodity hardware. This is in contrast to other stitching techniques that require cloud computing for timely processing. The processing speed eliminates the need for time-consuming uploading and downloading of large amounts of data, and makes it possible to keep all data local and secure.

Figure 11:
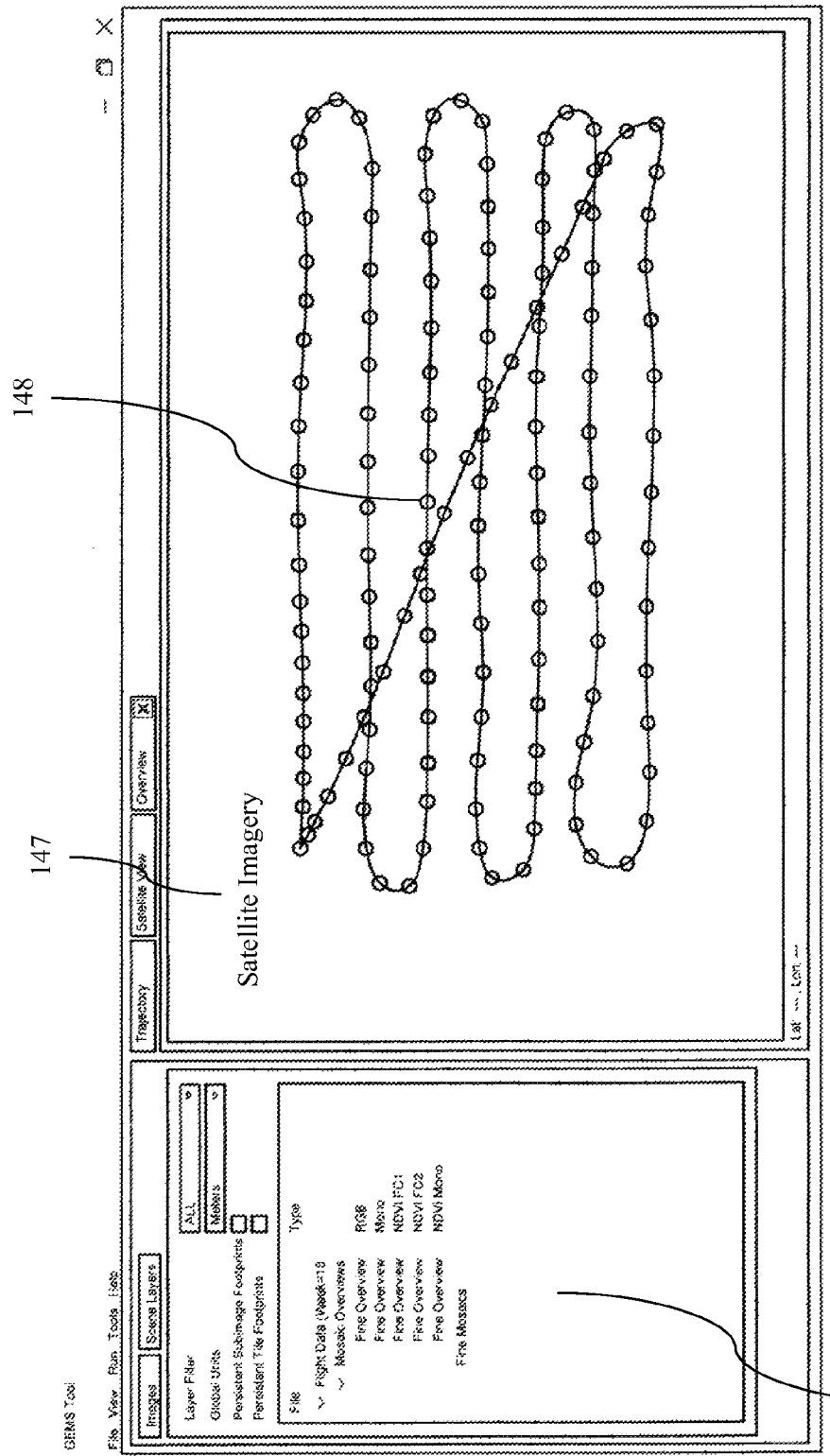
FIG. 11 depicts the software component of an embodiment, showing the main user interface and the vehicle flight trajectory over satellite imagery.
Figure 13:
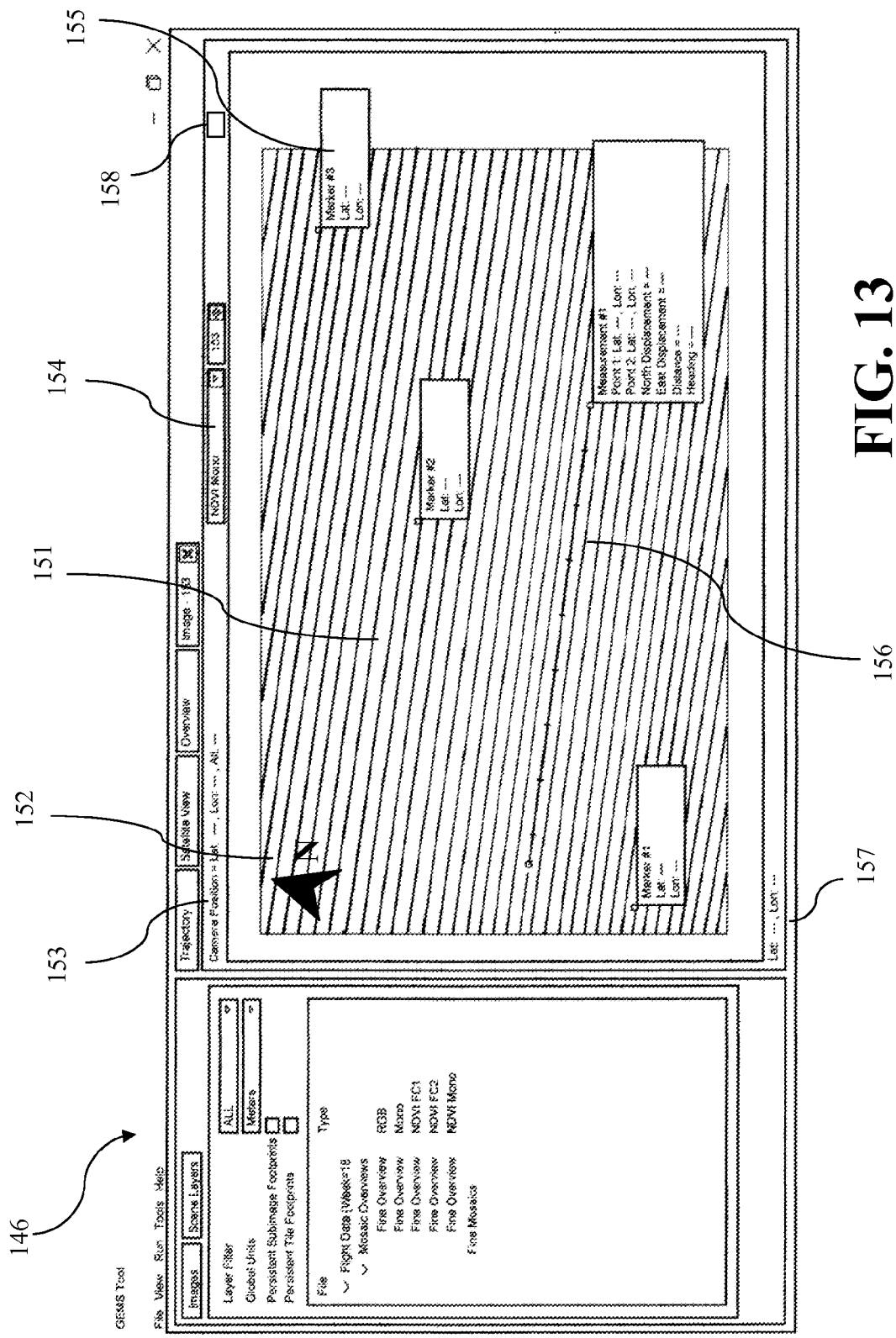
FIG. 13 depicts the software component of an embodiment, showing the main user interface and an individual NIR image with GPS markers and distances superimposed.

The post-processing software 146, of an embodiment of the invention is integrated with various farm management systems and Geographical Information Systems to streamline end user workflow and throughput. FIG. 11 depicts the post-processing software graphical user interface. Reference number 148 depicts a two-dimensional flight trajectory of the unmanned aerial vehicle where each circle on the trajectory indicates image acquisition events of the camera system when the RGB images and NIR images as well as the corresponding sensor data were collected. The flight trajectory is overlaid on satellite imagery 147 that provides the user a reference plane for image viewing. On the left-hand side of the graphical user interface is a navigation tree 149 for organizing the collected data and post-processed imagery. Once the imagery has been processed (RGB, NIR, and NDVI) the mosaiced imagery is stored and can be accessed by double clicking on the overview. In addition to the mosaiced overview images the post-processing software 146 provides access to all of the individual sub-images that were acquired in flight. A sub-image can be opened and viewed in the graphical user interface with additional information displayed. FIG. 13 depicts a sub-image and corresponding information that is displayed to the end user. Toggle filter 154 allows the user to toggle between the different types of imagery including RGB, NIR, and NDVI. Reference number 151 depicts a spectrally aligned NDVI sub-image as viewed in the graphical user interface. Reference number 153 illustrates the WGS84 latitude, longitude, and altitude coordinates of the UAV camera when the image was acquired. Reference number 157 illustrates the WGS84 latitude, longitude, and altitude coordinates of the pixel that the mouse is hovering over on each individual displayed image. Compass rose 152 is used for ease of use to indicate to the end user the orientation of a sub-image. Reference number 158 provides additional image information. On a per image basis the information includes: camera position (latitude, longitude, altitude), system attitude (yaw, pitch, roll), height above ground, camera speed over the ground, ground sampling distance (GSD), RGB and NIR camera parameters (camera exposure times, distance traveled during camera exposure time, and translational image smear). In the graphical user interface the software allows the user to place and store GPS markers that indicate a pixel WGS84 latitude and longitude as illustrated in 155. These GPS markers can be placed on points of interest in the mosaic overviews (RGB, NIR, NDVI) and on individual sub-images (RGB, NIR, NDVI) and exported to a CSV file to easily be accessed in third party tools and enable the end user to return to these marked areas on the ground. 156 illustrates that distances can be measured between two points on each individual sub-image (RGB, NIR, NDVI) and on mosaiced overviews (RGB, NIR, NDVI). These distances can be exported to a CSV file for use in third party tools.

Embodiments comprise several distinct improvements over conventional systems, including:
1. Fully integrating navigation sensors and imaging sensors allows for geo-registering imagery without requiring integration with external systems (i.e. autopilot, nav systems, etc). The integration of these on-board sensors allow the system to detect UAV take-off and landing and start/stop recording accordingly, simplifying user interaction.
2. A novel method of aligning imagery from different cameras that are sensitive to different spectral bands.
3. A novel method of using the integrated navigation sensors to dynamically control and optimize camera settings in flight.
4. Novel techniques in image stitching and compositing that exploit the integrated navigation sensors to improve processing speed and robustness.
5. A utility to use the invention to evaluate the noise environment of a UAV and pinpoint potential interference sources.

Embodiments bring together navigation sensors, which are typically only found in the mission-critical avionics of a UAV, and imaging sensors and optics to form a self-contained UAV sensor payload. As a result of this union, embodiments are able to perform direct geo-referencing (estimating the GPS coordinates of each pixel in an image) without needing additional data from external systems, like an auto-pilot. Instead, they rely entirely on built-in sensors, which are aligned with the cameras and internally time synchronized to better than 1 ms with the camera trigger times.

Embodiments integrate all sensors on a rigid body so that the relative orientation of each sensor can be estimated in a calibration procedure that is performed before integration with an air vehicle. The cameras can be radiometrically characterized across all spectral bands and exposure settings. These characterizations relate camera digital number (DN) to at-sensor irradiance (uW/cm^2/nm) and to surface reflectance using an on-board incident light sensor or ground-based reflectance standards. The navigation sensors can be calibrated to compensate for sensor biases, scale factors, and misalignments, as well as for hard and soft iron anomalies. The advanced sensor calibration procedure employed by the present invention can improve raw sensor accuracy sixty fold over uncalibrated performance in some embodiments. In alternative designs (not the current invention), where the imagers are separated from the navigation sensors, estimating relative orientation of the different components and correcting for iron anomalies cannot be done before installation in the UAV. Inventive embodiments, in contrast, relieve the UAV integrator of the burdens of sensor synchronization and integration, sensor and camera alignment, and calibration.

All multi-spectral cameras that use multiple imaging sensors and optics are faced with the problem that the images from the different sensors are not perfectly aligned. That is, pixel (x,y) in an image from one camera and pixel (x,y) in an image from another camera from the same instant in time will not generally correspond to the exact same patch of ground. This problem is often combated by placing the imaging sensors as close to each other as possible, and by physically aligning the optics.

It is implicitly assumed, when computing crop spectral vegetation indices (SVIS), that the reflectance values from different spectral bands used in the computation of the index originate from the same location in space (i.e. patch of ground). In practice, this is very difficult to achieve for multi-camera sensors, particularly as the ground sampling distance (GSD) of the cameras decreases in size (i.e. increase in camera resolution). This is due to camera-to-camera orientation and displacement errors which may change over time due to shock, vibration, or impact events. Even if multi-camera systems are initially factory aligned, that alignment will only be valid for some amount of time or use. Additionally, factory alignment cannot compensate for spectral misalignment due to the perspective effect, which depends on the sensors constantly changing height above the ground.

Embodiments described herein utilize factory alignment techniques, but also use image processing techniques to estimate the remaining misalignment (due to the perspective effect and changes in optical alignment). The software component uses these estimates to compensate for the residual spectral misalignment when producing vegetation indices, achieving sub-pixel level alignment accuracy at all altitudes and ground sampling distances (GSDs). This ensures that crop and soil pixels are not mixed when computing multi-band, multi-camera spectral vegetation indices such as the Normalized Difference Vegetation Index (NDVI) or any other multi-band index.

Motion blur is caused by camera motion during the image exposure time. The footprint on the ground of a single pixel in the camera focal plane array is known as the ground sampling distance (GSD). If the camera moves a distance greater than 1 GSD during the camera exposure time then the patch of ground that an individual pixel sees at the beginning of the exposure interval is different than the patch of ground seen at the end of the exposure interval, resulting in blurring of the imagery. For example, for a UAV traveling at 30 knots (i.e. 15 m/s) and a camera exposure time of 1 millisecond, the camera will move 1.5 cm during the camera exposure time. The motion blur (measured in pixels) is equal to the platform speed times the camera exposure time divided by the camera GSD. Motion blurs of less than 1 pixel are desirable for image clarity.

Embodiments use the on-board navigation sensors to maintain accurate, up-to-date estimates of height above ground and vehicle ground speed. These can be used to predict the quality of imagery that can be collected with various camera settings (e.g. exposure settings). Embodiments can then weigh the advantages and disadvantages of different camera settings in terms of motion blur, over/under-exposure, and shutter efficiency, and select settings that will result in the best overall imagery. These settings can be continuously updated during data collection to maintain the best possible image quality, as needed.

In embodiments, a software component that processes the data collected from a UAV flight can be incorporated, as described previously. This software automatically stitches images into photo-mosaics and registers the mosaics against an absolute geodetic coordinate system. It can also produce registered, mosaiced vegetation indices from the raw image data and false-color visualizations of these indices. The software makes use of several innovations in image and data processing to provide timely and robust results.

Feature extraction and matching can be used to estimate how different pairs of images are aligned with one another. The system can use its navigation solution to predict where each feature in one image should lie in another. We call this alignment prediction. The present invention makes use of the highest-accuracy observables available from the built-in navigation system when performing alignment prediction. The system uses correspondence screening to compare each feature in one image with only the features in the other image that are consistent with the prediction. Unlike similar existing solutions, the present invention does this in a multi-hypothesis fashion to get the most out of the alignment predictions, regardless of the level of interference the sensor is exposed to. Using the navigation solution to perform alignment prediction and correspondence screening dramatically reduces the number of candidate feature correspondences that must be considered when aligning images. This reduction in the search space can reduce the execution time of image stitching from many hours to a matter of minutes. Additionally, alignment predictions from the navigation system are used in place of photogrammetric measurements when such measurements are not available. This improves the overall reliability of the stitching process because instead of dropping non-alignable images, the system seamlessly falls back on direct geo-referencing when needed.

A quantity that is needed for alignment prediction is a good estimate of the sensors height above the ground. Embodiments can incorporate one or multiple sensors, including GPS and barometric pressure, to maintain an estimate of height above ground that is several times more accurate and more stable than would be available from GPS alone.

In a conventional image stitching system, one must perform pose recovery, feature triangulation, and bundle adjustment to construct the final output. Embodiments described herein make use of a different processing pipeline that uses a reduced-order state space to accelerate processing. They use a novel pose recovery technique that makes use of photogrammetric measurements, as well as measurements from the integrated navigation system. This image stitching solution, which combines the navigation solution with feature matching, enjoys greater speed and reliability than other, purely feature-based image stitching methods.

The fact that embodiments described herein incorporate all sensors into a single stand-alone system makes it possible to use those embodiments to assess the noise environment on a given UAV. A preferred embodiment of the invention includes a software utility to plot raw sensor data from all on-board sensors and it superimposes target noise bounds on a per-sensor basis. It also plots GPS satellite signal strengths and position and velocity data. GPS satellite signal strengths enable an immediate diagnosis of electromagnetic interference on the UAV platform. The utility has built-in tools for assessing the impact of interfering sources. The systems described herein can be used to measure the angle between the magnetic field vector at different instants in time and the tool can plot the magnitude of the magnetic field as a function of time. This makes it possible to quickly detect hard and soft iron anomalies on a UAV.

In embodiments, a self-contained unmanned aerial vehicle sensor payload for precision agriculture includes a plurality of sensors mounted within a housing, the plurality of sensors including a tri-axial gyroscope, a tri-axial accelerometer, a tri-axial magnetometer, pressure transducers, temperature sensors, a GNSS receiver, an image sensor sensitive to near-infrared (NIR), an image sensor sensitive to red-green-blue (RGB), and an integrated processor. The integrated core processor or PC-based processing software computes the position and orientation of the cameras at each image acquisition time using the navigation sensor data, spectrally aligns images using factory alignment and image processing techniques, computes vegetation indices using the aligned spectral image data, stitches the RGB, NIR, and vegetation index images into mosaics using the computed position and orientation data and feature matching methods, and geo-registers the images and RGB, NIR, and NDVI mosaics to a geodetic reference system.

In such UAV's, the GNSS receiver can be a standard GPS receiver, a differential GPS receiver, an RTK GPS receiver, a Galileo, Glonass, or other constellation receiver or a multi-constellation receiver. An additional incident light sensor can be used to measure incident irradiance, for use in computing surface reflectance. The plurality of sensors can be configured to detect take-off and landing events and autonomously begin and terminate recording accordingly (for example, begin recording at take-off and terminate recording at landing). In an embodiment, the plurality of sensors can be configured to begin and stop recording when a signal is received from an external source, or where images are collected on demand according to an externally provided trigger signal. The processing software is configured to conduct multi-threading and/or GPU acceleration to accelerate the computing, geo-registering, and stitching. Embodiments use real-time navigation data to continually optimize camera settings. The RGB and NIR imagery can be aligned through a combination of sensor factory alignment, and image processing which estimates the residual misalignment due to changing perspective and physical changes in sensor alignment that can occur as the sensor ages. The plurality of sensors can be configured to determine a navigation solution to compute prior estimates of image geo-registration and image alignment. The processing software and hardware can be configured to utilize these prior estimates to screen feature correspondences in data provided by the image sensors. Prior-based correspondence screening can be performed in a multi-hypothesis framework to dynamically determine alignment prediction accuracy. The image sensors can include associated lenses and optical filters, the lenses and filters being radiometrically characterized to produce vegetation indices that are consistent across multiple camera settings. The plurality of sensors can produce navigation measurements to generate system pose estimates and to support stitching. Image alignment prediction utilizes multiple sensors including GPS and barometric pressure to maintain an estimate of height above ground that is several times more accurate and more stable than would be available from GPS alone. A software module can be used to assess the noise environment on a UAV, including (for instance, but not limited to) vibrational noise, EMI, and magnetic interference due to soft or hard iron anomalies or nearby electrical currents.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:
1. A system for use in precision agriculture comprising:
   a. a self-contained unmanned aerial vehicle (UAV) sensor payload including:
      i. a plurality of sensors including gyroscopes, accelerometers, magnetometers, and a GNSS receiver,
      ii. an image sensor sensitive to near-infrared (NIR),
      iii. an image sensor sensitive to red-green-blue (RGB), iv. an integrated processor and supporting hardware, wherein all sensors are time-synchronized and co-located, and the relative orientations of the sensors are known;

b. on-board or off-board hardware and software configured to:

i. compute position and attitude estimates of the self-contained unmanned aerial vehicle (UAV) sensor payload at each instant images are collected by the NIR and RGB imager sensors a(ii) and a(iii) using data from the time-synchronized and co-located plurality of sensors in a(i), ii. determine a transformation between NIR and RGB imagery from the co-located and time-synchronized NIR and RGB image sensor a(ii) and a(iii) that maps a projection of each scene point in an image from one of the image sensors to a projection of the same point in an image from the other image sensor, iii. compute vegetation indices using the NIR and RGB imagery obtained by the NIR and RBG image sensor a(ii) and a(iii) using the transformation from b(ii), iv. use the computed position and attitude estimates from b(i) and the known relative orientations of the NIR and RGB image sensors a(ii) and a(iii) relative to the plurality of sensors in a(i) to geo-register and stitch the RGB and NIR imagery and the computed vegetation indices from (b)(iii).

2. The system according to claim 1 wherein the GNSS receiver is a standard GPS receiver.

3. The system according to claim 1 wherein the GNSS receiver is a differential GPS receiver.

4. The system according to claim 1 wherein the GNSS receiver is an RTK GPS receiver.

5. The system according to claim 1 wherein the GNSS receiver is a Galileo, Glonass, or other constellation receiver or a multi-constellation receiver.

6. The system according to claim 1 wherein an incident light sensor is used to measure incident irradiance, for use in computing surface reflectance.

7. The system according to claim 1 wherein the plurality of sensors and the onboard processor are configured to detect take-off and landing events and autonomously begin recording at take-off and terminates recording at landing.

8. The system according to claim 1 wherein the plurality of sensors and the onboard processor are configured to begin and stop recording when a signal is received from an external source, or where images are collected on demand according to an externally provided trigger signal.

9. The system according to claim 1 wherein multi-threading and/or GPU acceleration is used to accelerate the processing.

10. The system according to claim 1 wherein the processor uses real-time navigation data to continually optimize camera settings.

11. The system according to claim 1 wherein sub-pixel level spectral alignment is achieved at all altitudes through a combination of factory alignment and image processing that produces an estimate of residual misalignment due to physical hardware changes over time and changing perspective.

12. The system according to claim 1 wherein the processor or separate computer is configured to use the navigation solution to compute prior estimates of image geo-registration and image alignment.

13. The system according to claim 1 wherein prior estimates of image alignment are used to screen possible feature correspondences to accelerate and improve robustness of image stitching.

14. The system according to claim 1 wherein prior-based correspondence screening is performed in a multi-hypothesis framework to dynamically determine alignment prediction accuracy.

15. The system according to claim 1 wherein the image sensors and associated lenses and optical filters are radiometrically characterized to produce vegetation indices that are consistent across multiple camera settings.

16. The system according to claim 1 wherein navigation measurements are used in place of uncomputable or unreliable photogrammetric measurements for system pose recovery and to perform stitching.

17. The system according to claim 1 wherein sensor height above ground is estimated by computing changes in GNSS altitude and stabilized using additional on-board sensors.

18. The system according to claim 1 wherein a software module is used to assess the noise environment on the UAV, including vibrational noise, EMI, and magnetic interference due to soft or hard iron anomalies or nearby electrical currents.

* * * * *

UNITED STATES PATENT AND TRADEMARK OFFICE
CERTIFICATE OF CORRECTION

| | |
|---|---|
| PATENT NO. | : 9,945,828 B1 |
| APPLICATION NO. | : 14/921335 |
| DATED | : April 17, 2018 |
| INVENTOR(S) | : Poling et al. |

It is certified that error appears in the above-identified patent and that said Letters Patent is hereby corrected as shown below:

In the Specification

Column 6, Line 33, please delete "nay" and insert in its place --nav--.

Signed and Sealed this
Twenty-first Day of August, 2018

Andrei Iancu
*Director of the United States Patent and Trademark Office*